(12) United States Patent
Wolfe

(10) Patent No.: US 7,454,295 B2
(45) Date of Patent: *Nov. 18, 2008

(54) ANTI-TERRORISM WATER QUALITY MONITORING SYSTEM

(75) Inventor: Thomas D. Wolfe, Rough and Ready, CA (US)

(73) Assignee: The Watereye Corporation, Grass Valley, CA (US)

( * ) Notice: Subject to any disclaimer, the term of this patent is extended or adjusted under 35 U.S.C. 154(b) by 1221 days.

This patent is subject to a terminal disclaimer.

(21) Appl. No.: 10/392,112

(22) Filed: Mar. 19, 2003

(65) Prior Publication Data

US 2004/0006513 A1    Jan. 8, 2004

Related U.S. Application Data

(63) Continuation-in-part of application No. 10/055,225, filed on Oct. 26, 2001, now Pat. No. 6,560,543, which is a continuation-in-part of application No. 09/213,781, filed on Dec. 17, 1998, now Pat. No. 6,332,110.

(51) Int. Cl.
 *G01N 31/00* (2006.01)
 *G06F 19/00* (2006.01)

(52) U.S. Cl. ............................. 702/22; 702/30; 702/31; 700/270; 700/271; 210/141; 210/634; 210/638; 210/660

(58) Field of Classification Search .................. 702/22, 702/30–31, 188; 700/270, 271; 210/141, 210/634, 638, 660
 See application file for complete search history.

(56) References Cited

U.S. PATENT DOCUMENTS

| | | | |
|---|---|---|---|
| 4,830,757 A | 5/1989 | Lynch et al. | |
| 5,492,632 A | 2/1996 | Reber | |
| 5,608,171 A | 3/1997 | Hunter et al. | |
| 5,631,744 A | 5/1997 | Takeuchi et al. | |
| 5,832,410 A | 11/1998 | Lin et al. | |
| 5,835,724 A | 11/1998 | Smith | |
| 5,865,718 A | 2/1999 | Chan | |
| 5,970,426 A | 10/1999 | Mandel et al. | |
| 5,993,662 A | 11/1999 | Garr et al. | |
| 6,023,223 A | 2/2000 | Baxter, Jr. | |
| 6,061,603 A | 5/2000 | Papadopoulos et al. | |
| 6,305,944 B1 | 10/2001 | Henry et al. | |
| 6,317,639 B1 | 11/2001 | Hansen | |
| 6,332,110 B1 * | 12/2001 | Wolfe .......................... 702/22 |
| 6,356,205 B1 | 3/2002 | Salvo et al. | |

(Continued)

FOREIGN PATENT DOCUMENTS

WO    WO 01/80494    10/2001

*Primary Examiner*—John E. Barlow
*Assistant Examiner*—Hien X Vo
(74) *Attorney, Agent, or Firm*—McHale & Slavin, P.A.

(57) ABSTRACT

An Anti-Terrorism water quality monitoring system for continuously monitoring a potable water treatment system and related potable water distribution network that provides potable water to a municipality, city, housing development or other potable water consumer. The system includes the collection of data from the water distribution system and from the water treatment facility and from advanced separation processes which are integrated into analytical instruments. The data collected are stored in a remote database on a remote server computer or bank of computers and accessible by Homeland Security or its designated agency. Preferred parameters of monitoring include the turbidity and disinfectant such as chlorine, hypochlorous acid, sodium hypochlorite, calcium hypochlorite, ozone, chlorine dioxide, chloramines, hydrogen peroxide, peracetic acid.

32 Claims, 1 Drawing Sheet

U.S. PATENT DOCUMENTS

| | | |
|---|---|---|
| 6,370,448 B1 | 4/2002 | Eryurek |
| 6,389,331 B1 | 5/2002 | Jensen et al. |
| 6,560,543 B2 * | 5/2003 | Wolfe et al. .................. 702/22 |
| 2001/0020195 A1 | 9/2001 | Patel et al. |
| 2001/0053992 A1 | 12/2001 | Eto et al. |
| 2002/0023479 A1 | 2/2002 | Burge et al. |
| 2002/0130069 A1 | 9/2002 | Moskoff |
| 2002/0133270 A1 | 9/2002 | Hung et al. |

* cited by examiner

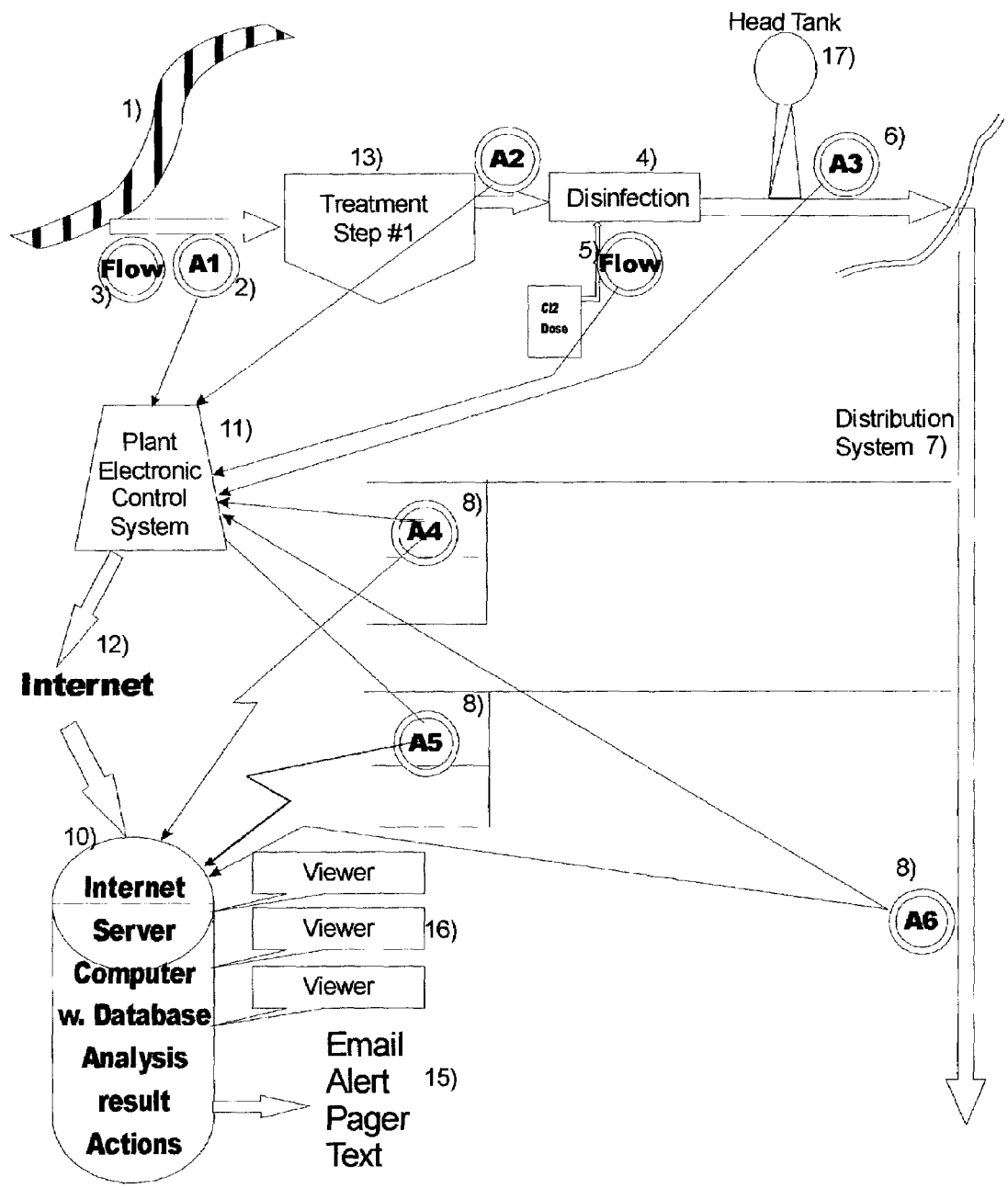

ANTI-TERRORISM WATER QUALITY MONITORING SYSTEM

RELATED APPLICATION

This Application is a continuation-in-part application of Ser. No. 10/055,225 filed Oct. 26, 2001 now U.S. Pat. No. 6,560,543 which is a continuation-in-part of Ser. No. 09/213,781 filed Dec. 17, 1998 issued Dec. 18, 2001 as Registration U.S. Pat. No. 6,332,110, the contents of which are incorporated herein by reference.

FIELD OF THE INVENTION

This invention is related to the field of water treatment, and in particular, to a method of monitoring advanced separation and/or ion exchange processes by use of the world wide web allowing review of data collected and compiled asynchronously from a web server.

BACKGROUND OF THE INVENTION

Protection of water supplies from either inadvertent or deliberate contamination is an increasingly important concern. While there exist many different devices and methods to analyze water for contaminants, widespread deployment of such devices is expensive and difficult.

Most water treatment and distribution systems rely on the introduction and maintenance of a disinfectant into the water system to protect against biological and to a big extent chemical contamination. Chlorine, in the form of gas or hypochlorite, is by far the most common material used for this purpose. However, substitutes such as chloramines, ozone, hydrogen peroxide, peracetic acid, chlorine dioxide, and various mixed oxides also find service in this application. All of these materials have a more or less common mode of action. They rely on some sort of oxidation to effect the deactivation of biological organisms and the destruction of other organic compounds present in the water to be treated. The reaction rates of the various disinfection compounds are reasonably well known and well characterized.

Additionally, the presence or absence of turbidity in the water supply can greatly affect the amount of disinfectant required to achieve inactivation of biological organisms. The suspended particles producing turbidity are usually removed in the water treatment process before disinfection agents are applied. However, turbidity breakthroughs do occur and failure to quickly raise the disinfection dose level can lead to insufficient disinfection residuals reaching the distribution system. This can present a threat to public health, particularly if the drinking water supply is contaminated either deliberately or inadvertently.

To respond to the threats of terrorism in drinking water supplies, sensors have been and are being introduced into the distribution system to continuously monitor selected contaminants in the drinking water supply. For example a system may monitor free chlorine residual at a location in the distribution system downstream of the main treatment plant. However, the concentration of free chlorine present at this point in the distribution system may lag the free chlorine analyzed at the exit of the water treatment plant by hours or even days in some cases. The lag will also vary by time of day, since water demand follows well known 24 hour cyclical periods.

Applicant's invention registered as U.S. Pat. No. 6,332,110 teaches the use of a remote monitoring system to monitor the performance of an advanced separation process, particularly as related to water treatment. Many of the analytical devices used to continuously monitor water treatment operations are based on advanced separation processes employing selective ion membranes which concentrate the analyte for the detector apparatus. For example, detection of chlorine may be mediated via a membrane which readily and specifically passes free chlorine or hypochlorous acid (HOCl), thus separating the analyte from the bulk solution and concentrating it. The detector apparatus may incorporate multiple sensors and analyzers on a single unit. The multiple units are usually electronically controlled. The control system usually features output methods allowing the display and storage of collected data.

Deploying a range of sensor systems in the field provides a means to analyze for contaminants but does not provide for reporting and subsequent analysis of the data. Rapid reporting of the data to a facility readily accessible by the management or operators of the utility or distribution system and subsequent analysis of the data is very important to providing quick response in the event of a system contamination, either deliberate or otherwise.

The instant invention provides a means of rapidly aggregating the information at a central location in a form readily accessible to authorized users such as Homeland Security. It further provides a means to employ sophisticated statistical and data analysis techniques to the collected data. Since the central data collection server is connected to the internet, dispersion of alarms and alerts is greatly facilitated.

This invention consists of a method for collecting analytical data from the electronic control system of a single analyzer unit or multiple analyte units, storing the raw data locally for a short period of time, and subsequently using any of a variety of transmission means to send this data to a remote internet server computer. At the remote internet server computer, the data is stored in a database and may also be displayed via a web server. Upon arrival, or upon scheduled intervals, or upon a user request, the data is analyzed, compared to historical records, and a performance analysis result is made. Based upon the raw data or upon the analysis result, reports can be issued to appropriate regulatory agencies, alerts or alarms can be raised, and notifications issued via email, pager, voice or text messaging, or other messaging medium which can be mediated by a computer program connected to a phone line or the internet.

The methods used for data analysis can be readily varied or modified by someone skilled in the art of computer programming since the raw data is easily available from the database for manipulation. For example, the analytical data, when combined with known system constants such as flow rates, residence times, and so on, can be used to continuously generate a calculated product of disinfectant concentration times contact time C*T. This simple factor alone is quite useful in predicting the amount of biological organism deactivation. More sophisticated analyses can also be utilized. The results can be conveniently stored in the database and displayed as virtual sensors.

This invention is particularly useful when the same remote server computer has access to data from both the treatment facility and to analytical data from within the distribution system. In this case, historical information can be used to predict the expected conditions within the distribution system based on the effluent conditions from the treatment plant. The expected conditions can then be compared to the actual conditions in the distribution system. For example, in the instant invention, assume that data is being collected at the water treatment plant from the electronic control system about water flow rates, chemical dosing rates, filtered water turbidity, and chlorine residual. Also assume that data is also being collected from sensors in the distribution system reporting chlorine residual among other data. With current data and with historical data as a reference point, one can calculate a chlorine demand from the chemical dose rates, flows, and residual. Chlorine Demand is the actual amount of chlorine which is reacting, typically calculated as free chlorine dosed less the residual. Chlorine demand can be correlated with temperature, season, and filtered water turbidity. Additionally residual chlorine leaving the plant can be correlated with residual chlorine within the distribution system. If the actual chlorine residual measured at the distribution system point of measurement varies from the historical values expected from the chlorine residual leaving the treatment facility by more than a set percentage or more than a set number of standard deviations, then an alarm or alert may be issued by the monitoring system of the instant invention.

As a further example, consider the potential deliberate injection of chemically or biologically active agents into the distribution system at a point downstream of the treatment facility. A sophisticated terrorist may first inject a chlorine scavenger such as sodium metabisulfite into the distribution system to eliminate the chlorine residual normally present. At some point downstream of the metabisulfite injection point, the chemical or biological agent can be injected into the water without destruction by any residual disinfectant. Without an analytical station and monitoring system in place within the distribution system this approach could go undetected for quite some time, allowing a thorough infiltration of a biological or chemical agent throughout the distribution system. Assuming such an attack, the chlorine residual at the monitoring station would very quickly diminish to zero. A monitoring system with an active system in place to analyze the incoming data would quickly detect such an attack and sound the alarm. With historical data to compare to, the incidence of false terrorist attack alarms could be greatly diminished. For example a chlorine dosing equipment failure would be noticed at the water treatment plant providing information that a subsequent fall of chlorine concentration in the distribution system was not a terrorist attack, but an equipment failure.

In the same example of a hypothetical terrorist attack, the terrorist might try to simply overwhelm the residual chlorine in the distribution system by injecting, for example, an amount of biological or chemical agent dispersed as a fine powder in water. In this case, chlorine would fall as well but depending on the location of the sensors in relation to the injection point, the concentration might not fall to zero. However, the turbidity might well be affected. Thus a turbidity sensor in the distribution system would be an advantage in assessing a potential threat. In all cases, the need to quickly transmit raw data from both the distribution system and treatment plant to a computer system where it can be manipulated and analyzed is very important for prompt action to occur in response to any threat to the water system.

SUMMARY OF THE INVENTION

The instant invention is a method for continuously monitoring a water treatment system and related distribution network providing potable water to a municipality, city, housing development or other potable water consumer. The method includes the collection of data from the distribution system and in the preferred embodiment from the water treatment facility as well. The method also includes the collection of data from advanced separation processes which are integrated into analytical instruments. The data collected are stored in a remote database on a remote server computer or bank of computers.

The data are manipulated to generate preconfigured performance, maintenance, quality assurance, quality control, regulatory, performance graphing, historical trends, and regulatory reports. The data is collected from sensors located at an equipment site and transferred to a remotely located computer using transmission means by use of the Internet where all data received can be used for the generation of reports which are accessible by Internet connection. The reports, graphs and information can be viewed online or downloaded by use of a web browser. Regulatory reports can be forwarded automatically to the regulatory agency via electronic transmission means with the added benefit of receiving reports generated directly from the sensor input thereby eliminated the possibility of human error or tampering. The method allows a single location to monitor countless customers with each customer capable of reviewing information relevant to their equipment. All information is kept confidential by use of appropriate account names, protocols and passwords.

Thus, an objective of the invention of utmost importance for security concerns is to use the data manipulation steps to continuously compare the current water treatment facility data with current data obtained from the distribution system to each other and to historical records of performance already stored in the database. As will be readily appreciated by those skilled in the art of data analysis, this can provide a powerful indicator of either normal response in the distribution system or out of bounds conditions that may require immediate notification of responsible parties preferrably by direct contact with Homeland Security.

Another objective of the invention is to provide a means for analytical devices using advanced separation processes such as ion selective membranes or electrodialysis membranes to rapidly and securely transmit their data to a remote database server computer for data manipulation and display on the World Wide Web.

Another objective of the invention is to provide a facile means to evaluate the conditions in the water treatment distribution systems as to health and safety concerns and allow this information to be shared by responsible parties via the World Wide Web.

Yet another feature and objective of the invention is to provide a means of remote monitoring advanced separation processes, water, and wastewater treatment plants in a manner that prevents any possible hacker attack to the electronic control system of the plant or process being monitored. The use of a remote database and web server allows viewers near real time access to plant performance but only allows access to web pages, not the control system. In more conventional remote monitoring applications, users or viewers need to actually connect with the computer or electronic control system which is actually controlling the plant. Thus, compromised passwords could result in an unauthorized user seizing control of the control system. In the instant invention, the control system need not be configured for remote access at all. In the instant invention, a compromised password will merely allow a remote user to see data from the process but not control any part of process, nor actually make any connection to the electronic control system of the facility, or computer attached to the electronic control system.

BRIEF DESCRIPTION OF THE DRAWING

FIG. 1 is a flow diagram of a conventional water treatment facility and distribution system with the interfaced anti-terrorism quality monitoring system of the instant invention.

DETAILED DESCRIPTION OF THE PREFERRED EMBODIMENT

Referring to FIG. 1, which shows a typical water treatment facility and distribution system, water from the supply (1) is pumped to the treatment plant. Analyzer A1 (2) and flow meter (3) collect data on the raw water supply. Analyzer A1, analyzing for turbidity, temperature, and possibly TOC (Total Organic Carbon) are not strictly necessary but if present provide better predictive reliability.

Treatment step (13) typically consists of settling and filtration to remove suspend matter. Analyzer A2 (14) monitors the efficiency of the treatment step. Disinfection step (4) allows chlorine dosed from the chlorine dosing station (5) to contact the water for a period of time, variable depending on temperature and organic matter loading in the supply water. Analyzer A3 (6) verifies that the disinfection step is working by measuring chlorine residual before entering the distribution system (7).

Analyzers A4, A5, and A6 (8) analyze for chlorine residual in the distribution system. Multifunction analyzers, the so called ab on a chip could also be used in the distribution system to analyze for constituents in addition to chlorine.

Data from the water treatment system is typically collected by a SCADA or other electronic control system (11) allowing local operators to operate and control the plant. Analyzers in the distribution system can be fitted to either send data to the treatment plant SCADA system or to the remote Database and Web Servers (10) of the instant invention. Data sending can be via transmission methods to the internet then subsequently via the internet to said remote database and web servers.

At the said remote database and web servers, the data is manipulated, reported, and displayed for various authorized viewers and users (16). If the data manipulation indicates that alarms or alerts are warranted, the software in the database can send the appropriate notices (15).

As can be readily appreciated there are many different permutations and combinations of the above system which will be obvious to someone skilled in the art of water treatment and in the art of remote monitoring. No matter the permutations, key features of the instant invention remain the same. For example, the distribution system may incorporate various additional pumping stations or head tanks (17). Similarly, the transmission methods used by the instruments and analyzers in the water treatment system and in the water distribution system used to send data to either the remote database and web servers or to the SCADA system at the treatment facility can vary. For example cellular phones can be used to dial either local or central internet services providers. Radios, or so called remote terminal units (RTU) coupled to radio frequency transmitters, can also be used to send transfer the collected data to SCADA system or can send it directly to the said remote database.

I claim:

1. An anti-terrorism monitoring system that provides for the remote monitoring of a potable water treatment system performance parameters and associated potable water distribution system that employs electronic controls, said monitoring system comprising the steps of:

a) accessing raw operating and performance data from said electronic controls;

b) providing a storage means on a local computer for holding said raw operating data in an electronic format;

c) coupling said local computer to an Internet server computer;

d) transmitting said stored raw data via the world wide web using transmission methods to a remotely located Internet server computer;

e) storing said raw data on said Internet server computer;

f) accessing such data asynchronously from said Internet server;

g) manipulating said raw data into an analysis result and report result;

h) comparing selected performance parameters within said portable water treatment system against selected performance parameters within said portable water distribution system to produce a comparison analysis result;

i) uploading said analysis, comparisons and said report results to an Internet server in a format suitable for access and visualization with a web browser program.

2. The method of claim 1, further including the step of filing said report result with Homeland Security or a designed terrorism reporting agency.

3. The method of claim 1, further including the step of transmitting said report result directly to Homeland Security or a designated terrorism reporting agency using electronic transmission means.

4. The method of claim 3, wherein said electronic transmission means is via e-mail.

5. The method of claim 3, wherein said electronic transmission means is via ftp (file transfer protocol).

6. The method of claim 3, wherein said electronic transmission means is via direct connection over the internet to a database located on a remote computer.

7. The method of claim 3, wherein said electronic transmission means is via cellular text or voice messaging means.

8. The method of claim 3, wherein said electronic transmission means is text to voice messaging using a modem.

9. The method of claim 1, wherein said step of manipulating said raw data includes routines to notify selected individuals on the basis of the stored parameters relating to the performance of the system being analyzed.

10. The method of claim 1, wherein said step of manipulating said raw data includes routines to notify selected individuals on the basis of the stored parameters relating to compliance testing dates and performance criteria.

11. The method of claim 1, wherein said step of accessing the raw data includes the steps of reading, querying, and storing data accessed from said electronic controls by use of a communications card interface.

12. The method of claim 1 wherein said step of accessing said data, storing said raw data locally, and transmitting said data to said remotely located internet server computer, is integrated into said electronic controls.

13. The method of claim 1 said electronic controls include a programmable logic controller (PLC).

14. The method of claim 1 wherein said step of accessing raw operating data from said electronic controls includes a serial interface coupled to said local computer, whereby said serial interface card is operable to transfer serial output of raw data from said electronic controls to the local computer.

15. The method of claim 1 wherein said step of accessing raw operating data from said electronic controls includes a USB enabled interface coupled to said local computer, whereby said USB enabled interface is operable to transfer output of raw data from said electronic controls to the local computer.

16. The method of claim 1 wherein said analysis result is a comparison between disinfectant concentration at said water treatment system and disinfectant concentration in said water distribution system.

17. The method of claim 1 wherein said analysis result is a comparison using algorithms to account for the known time lag between changes in the disinfectant concentration at said water treatment system and subsequent changes in the disinfectant concentration in said water distribution system.

18. The method of claim 1 wherein said analysis result is a comparison using algorithms to account for the known time lag between changes in the turbidity value at said water treatment system and subsequent changes in the turbidity in said water distribution system.

19. The method of claim 1 wherein said analysis result is a comparison of the turbidity and disinfectant values at said water treatment system and the turbidity and disinfectant values in said water distribution system.

20. The method of claim 1 wherein said analysis result comparison utilizes data manipulation routines to compare changes in disinfectant concentration in the distribution system to historical values stored in said internet server computer database.

21. The method of claim 1 wherein said performance parameters include:
 a) the concentration of disinfectant in the discharge water at the point of discharge from the water treatment plant; and
 b) the concentration of disinfectant in the discharge water at a distance greater than 100 meters from said point of discharge.

22. The method of claim 1 wherein said performance parameters include;
 a) the turbidity in the discharge water at the point of discharge from the water treatment plant; and
 b) the turbidity in the discharge water as measured at a distance greater than 100 meters from said point of discharge.

23. The method of claim 1, wherein said step of transmitting said data to said remotely located internet server computer is via earth satellite transmission methods.

24. The method of claim 1, wherein said step of transmitting said data to said remotely located internet server computer is via cellular telephone network transmission methods.

25. The method of claim 1, wherein said step of transmitting said data to said remotely located internet server computer is via radio frequency transmission methods.

26. The method of claim 1, wherein said step of transmitting said data to said remotely located internet server computer is via direct connection over the internet to a database located on a remote computer.

27. The method of claim 1, further including the steps of:
 i) comparing said analysis result with known optimum performance parameters, determining the differential between said known optimum performance parameters and the analysis result, and sending notifications to pre-determined recipients if known limits for differentials are exceeded;
 j) Determining the differentials between said known optimum performance parameters and the analysis result;
 k) Sending notifications to pre-determined recipients if known limits for said differentials are exceeded.

28. The method of claim 1, further including the steps of converting operating data into visual graphs.

29. The method of claim 1, further including the steps of converting operating data into statistical reports.

30. The method of claim 1, wherein the water treatment system incorporates the use of advanced separation processes in the determination of values of said performance parameters.

31. The method of claim 30, wherein the advanced separation process consists of an ion selective membrane used to at least partially separate the analyte from the bulk solution, a detector, and an electronic control system to control the detector and output results.

32. The method of claim 21 where said disinfectant is composed of at least one of the following: chlorine, hypochlorous acid, sodium hypochlorite, calcium hypochlorite, ozone, chlorine dioxide, chloramines, hydrogen peroxide, peracetic acid.

* * * * *

UNITED STATES PATENT AND TRADEMARK OFFICE
CERTIFICATE OF CORRECTION

| | | |
|---|---|---|
| PATENT NO. | : 7,454,295 B2 | Page 1 of 1 |
| APPLICATION NO. | : 10/392112 | |
| DATED | : November 18, 2008 | |
| INVENTOR(S) | : Thomas D. Wolfe | |

It is certified that error appears in the above-identified patent and that said Letters Patent is hereby corrected as shown below:

In claim 1, column 6, line 14, the phrase "portable water treatment system" should read as -- potable water treatment system --;

In claim 1, column 6, line 15, the phrase "portable water distribution system" should read as -- potable water distribution system --; and In claim 32, column 8, line 39, -- and -- should be inserted between "peroxide," and "peracetic acid."

Signed and Sealed this
Twenty-ninth Day of November, 2011

David J. Kappos
*Director of the United States Patent and Trademark Office*